US012781232B2

(12) United States Patent
Liu et al.

(10) Patent No.: US 12,781,232 B2
(45) Date of Patent: Nov. 3, 2026

(54) BACTERIAL CONTINUOUS EVOLUTION SYSTEM, ORTHOGONAL ERROR-PRONE DNA POLYMERASE, AND CONTINUOUS EVOLUTION METHOD

(71) Applicant: JIANGNAN UNIVERSITY, Wuxi (CN)

(72) Inventors: Yanfeng Liu, Wuxi (CN); Jian Chen, Wuxi (CN); Guocheng Du, Wuxi (CN); Long Liu, Wuxi (CN); Xueqin Lv, Wuxi (CN); Rongzhen Tian, Wuxi (CN); Runzhi Zhao, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 444 days.

(21) Appl. No.: 18/514,541

(22) Filed: Nov. 20, 2023

(65) Prior Publication Data

US 2024/0093212 A1 Mar. 21, 2024

Related U.S. Application Data

(63) Continuation of application No. PCT/CN2023/092743, filed on May 8, 2023.

(30) Foreign Application Priority Data

Aug. 24, 2022 (CN) ......................... 202211021222.2

(51) Int. Cl.
*C12N 15/75* (2006.01)
*C12N 9/12* (2006.01)

(52) U.S. Cl.
CPC ........... *C12N 15/75* (2013.01); *C12N 9/1252* (2013.01); *C12Y 207/07007* (2013.01); *C12N 2830/002* (2013.01)

(58) Field of Classification Search
None
See application file for complete search history.

(56) References Cited

FOREIGN PATENT DOCUMENTS

WO WO-2019079775 A2 * 4/2019 ............. C40B 40/08

* cited by examiner

*Primary Examiner* — Ekaterina Poliakova-Georgantas
(74) *Attorney, Agent, or Firm* — SZDC Law PC

(57) ABSTRACT

The present invention provides a bacterial continuous evolution system, an orthogonal error-prone DNA polymerase, and a continuous evolution method. In the present invention, by combining an orthogonal DNA replication system and an orthogonal error-prone DNA polymerase, a continuous evolution method that includes all mutant types, enables long-DNA-fragment mutation, and is good in continuity and simple and convenient to operate is obtained. By inducing the opening and closing of DNA polymerase expression, switching between a linear plasmid error-prone mutation process and a high-fidelity replication process is realized, so as to achieve the efficient and continuous evolution of a target DNA sequence.

9 Claims, 1 Drawing Sheet

Specification includes a Sequence Listing.

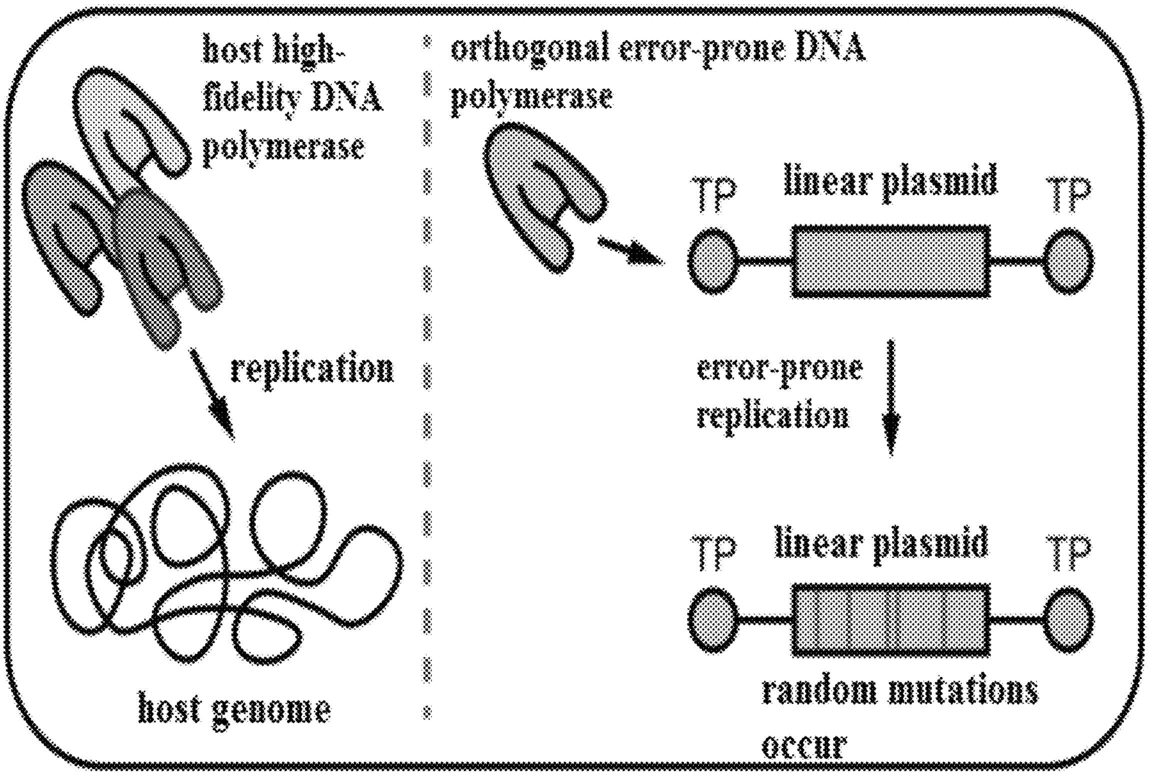
host high-fidelity DNA polymerase
replication
host genome
orthogonal error-prone DNA polymerase
TP
linear plasmid
TP
error-prone replication
TP
linear plasmid
TP
random mutations occur

SEQUENCE LISTING

```
Sequence total quantity: 24
SEQ ID NO: 1            moltype = AA  length = 734
FEATURE                 Location/Qualifiers
source                  1..734
                        mol_type = protein
                        organism = unidentified
SEQUENCE: 1
MSTTNRKKRR EIKLFTLDTE TRGLDGDVFR IGLFDGKQYY TGYTFADVLP VFEKYKAYDC  60
HVYIHNLDFD LSKIIAELRD YAEPTFNNSL FINGNIVTFT ASHIILHDSF RLLPSSLENL  120
CRDFDLLEGG KMDIVDYMEE NNYGIYNVKN RKLNKRLTKG NFFTTVDKDD PVLCEYMEYD  180
CRSLYKILEI VIGLSKLEVE QFINCPTTAS LAKTVYKEQY KKDYKVAIST KQYNHKQLGK  240
GLEAFIRKGY YGGRTEVFTP RIENGYHYDK NSLYPYVMKM AEMPVGYPNV LDNEEAELSF  300
DLWKRRRYGA GFIHAKVHVP EDMYIPILPK KDYTGKLIFP VGKIEGVWTF PELALAEAEG  360
CKIEKIESGV VFEKTAPVFR EFISYFEEIK NTSKGAKRAF SKLMQNALYG KFAMQRERIM  420
YADISERDKL EAEGHTVSEI IYDMNGIRME FLEYDGYAMA EYIQPHISAY ITSIARILLF  480
KGLKYAHEKG ILAYCDTDSC ATTTKFPDKM VHDKEYGKWK LEGYVIEGLY FQPKMYAEKA  540
INTDGEYEEV LRMKGVPKWV VEEQLDYNSF RKWYLQVKRG KAEIPIYKGG ERVQKFLTKS  600
KNNIEMNELA EMHKTINFAR EQKRNIDLNK NITSPLVRND YGENKDEKSE YEFDEWYERL  660
EEFNDDMNAV EELCMKFGKI QIPEKKQRKL YGLYKEYSSK AKAMCFSNEG LPIQDWCKKT  720
GWDMKELLGE LSFL                                                  734

SEQ ID NO: 2            moltype = DNA  length = 738
FEATURE                 Location/Qualifiers
source                  1..738
                        mol_type = other DNA
                        organism = unidentified
SEQUENCE: 2
atgaacaaaa atataaaata ttctcaaaac tttttaacga gtgaaaaagt actcaaccaa  60
ataataaaac aattgaattt aaaagaaacc gataccgttt acgaaattgg aacaggtaaa  120
gggcattaaa cgacgaaact ggctaaaata agtaaacagg taacgtctat tgaattagac  180
agtcatctat tcaacttatc gtcagaaaaa ttaaaactga atactcgtgt cactttaatt  240
caccaagata ttctacagtt tcaattccct aacaaacaga ggtataaaat tgttgggagt  300
attccttacc atttaagcac acaaattatt aaaaaagtgg tttttgaaag ccatgcgtct  360
gacatctatc tgattgttga agaaggattc tacaagcgta ccttggatat tcaccgaaca  420
ctagggttgc tcttgcacac tcaagtctcg attcagcaat tgcttaagct gccagcggaa  480
tgctttcatc ctaaaccaaa agtaaacagt gtcttaataa aacttacccg ccataccaca  540
gatgttccag ataaatattg gaagctatat acgtactttg tttcaaaatg ggtcaatcga  600
gaatatcgtc aactgtttac taaaaatcag tttcatcaag caatgaaaca cgccaaagta  660
aacaatttaa gtaccgttac ttatgagcaa gtattgtcta tttttaatag ttatctatta  720
```

```
tttaacggga ggaaataa                                                738

SEQ ID NO: 3            moltype = DNA  length = 7987
FEATURE                 Location/Qualifiers
source                  1..7987
                        mol_type = other DNA
                        organism = unidentified
SEQUENCE: 3
tatgtacctc tactagccta ttaaaatatt tacctattga cacgtaataa catttatgaa  60
atatgatata caaaatttc taaaattaac tattgacaat ttggaaaatt tattggaatt  120
tccaaaagga aaagtgtgac aagatattcc aagggtgcta taataggaaa tgagttgaaa  180
acgaacacgc gttttataga tgttcggttt ttgtaacata actgtaacat aaaaacattt  240
gcattactgg taactttcgg gtaatattgg tagcagagag ggacaaacgg gacaaatcga  300
gacacgatac atactctcta tacaagtgaa aagaaggtgg tgcatatgta atatgagtaa  360
actactgact gcgcaagagg ttgcagactt attgcgtgtt cataaaaaga ctatccatag  420
aatgatacat tctggaaagt tagacgcttc taaggtagca aacaaattcc ttattaaaga  480
ggaagatgca aaaggactat tggaaaataa aaataaaatg gacaattaat aggaggaata  540
ttcaatggaa aacaatacta aacaattaaa taatgaggtt aacgaaatcg cggtagtgga  600
cgagcatgta aatacaaatg acatcgtaac agtggacaag gtgtcacctt caatctttga  660
agcggacgga gcgaaggatg tattcttctc atctattcaa agtaaagatc gtaaatcagc  720
tatcaaagtt tataatgcta ttaactctag tgagaatgct ctagcagatc atagaggtga  780
agtattagaa atcacggaca tggttgctca tgctattact ctacaagatg aattgacaaa  840
agaagatgtg gatgcattac gtgttgtttt aattgataag aacggtaaag cataccacgc  900
ggtgtcacaa ggggtcgtat catctattca aaagattatt agtattgtag gtccagcacc  960
ttggaacgag cctttagaaa ttgttccggc agaagtgaaa acacgtaaag gatttaaaac  1020
attaactctt caactacaag gctaattttt gtaacaaatg aatgagggtg cacattgtgt  1080
atcctctttt ttaaaacata aaaggatggt gcggtcgtga acgctattaa aaacttagtt  1140
caagtatcta ttcggacaaa tgaacgagaa ctggaatttg tctcttttaa tggaatggtg  1200
catttgaagc aaaagttaga agaagatgaa acatccgtcg tgttaacaaa agaagagtta  1260
gacatggttg cagctatgtc taattttgat aatgtgatag ccaactttat gaactctatt  1320
acagaaaaga aagccatgta agccaaagac ctgtgaccta gttgttacgg gtcacatggc  1380
tttataagta ggtgatacaa tggcaaataa acggttaaag aagaaattag aaacgaaacg  1440
taaaaagtcg ttacttgttt cagaaggtta tagtaagaaa gaaacaaaga agctgaaagg  1500
tagagagtta gaaactgttt ataaaaagaa agcgcataat aggaaaaata gagagcgtgc  1560
tagggaaata gcaaatctag caagacagtg gggactttca ccgagtaagt ttaattcatg  1620
gaaaaagtta cttccggaaa tagagagaat aaaaaaagaa caagataggg aagcaccttt  1680
tctagtaata tactatcagg actttacagg tgagacagac agtaagttta tatatgattt  1740
taaaaagaga aacaatacaa gatcacgtag ccaaattact aggtctataa taggttggtt  1800
gcagaacgcc cagaacaaac tatttttagg aagggttgct atgcggattg tcccaaaacg  1860
tgatgtatct aaaaccaata cactttggaa gaatcacggc tatgtaaaga tatatgaggg  1920
acaaggaaaa gaacttacaa aactattaac agcaatagaa acgataatgg ttggtgttta  1980
cgacgtaaaa gaccgtgaca agtatttaaa gcagttatta aataatcttc gttccttacc  2040
atataaacaa gcacatagga acgctaatga gattcagaag atatatgata ctaaatcata  2100
tacgaaagaa agttgggata acgatgagta ctactaatag aaaaaagcgt agagagatta  2160
aactctttac gctagatact gaaacacgtg gtttggacgg cgacgtgttt cgaattggac  2220
tattcgatgg aaaacaatac tatactggct atacgtttgc agacgtatta ccagtgtttg  2280
aaaagtacaa agcatatgac tgtcatgtat atatacataa cctagacttc gacctttcca  2340
agatcatagc agagttacgt gattatgctg aaccaacatt taataactcg ctatttatca  2400
atggtaatat agtaacgttt accgcttctc atattatact acatgatagc ttccgattgc  2460
taccgtcttc acttgaaaac ttatgtagag atttcgacct tttagaaggt gggaagatgg  2520
atattgtcga ttatatggaa gaaaataatt acggtattta taatgtaaaa aaccgtaaat  2580
tgaacaagcg acttacaaaa ggtaatttct ttacaacagt agataaagat gaccctgtcc  2640
tatgtgagta catggaatat gattgtcgta gtttatataa aatcttggaa attgtaatag  2700
gcctatcaaa attagaagtt gaacaattta ttaattgtcc gactacagct tccctagcta  2760
aaacagttta taaagaacag tataagaagg attataaagt tgctatttct acaaaacaat  2820
ataatcataa acaactagga aaaggtttag aggcatttat tagaaaaggc tactatggag  2880
gaagaaccga agtttttaca ccaagaatag aaaacggata ccactatgat aaaaatagtt  2940
tatatccata tgttatgaaa atggctgaaa tgccagtcgg atacccgaat gtactggata  3000
atgaagaagc agaactttct tttgatctat ggaaaagaag aagatatgga gcaggcttta  3060
tacatgcgaa ggtacatgta cccgaagata tgtatattcc tatcttacct aaaaaagact  3120
atacaggtaa attgatttc ccagttggta aaatagaagg tgtttggaca tttccggaac  3180
tagctttagc agaagcggaa ggttgcaaaa tagaaaaaat cgaaagcggt gttgtatttg  3240
agaaaacagc acctgtcttt cgtgaattta tttcgtattt tgaggaaata aaaaatacaa  3300
gtaaaggtgc taaacgagcc ttttcaaaac ttatgcagaa tgcgttgtat ggaaaatttg  3360
caatgcagcg ggaacgaatc atgtatgctg atatttctga gagagataaa cttgaagcag  3420
aaggacatac agtaagcgag atcatatatg atatgaatgg aattcgaatg gaatttttag  3480
agtatgacgg atatgctatg gctgaatata ttcaaccaca tatttcagca tatattactt  3540
ctattgcaag aattctacta tttaaaggat tgaagtatgc gcatgaaaaa ggaattttgg  3600
cttattgtga tacggacagt tgtgcaacaa ctacgaaatt tcctgataaa atggttcacg  3660
ataaagagta tggaaagtgg aagttagaag ggtatgttat tgaaggactc tatttccaac  3720
caaaaatgta tgcggaaaaa gctattaata ccgatggtga atatgaggaa gtattacgaa  3780
tgaaaggtgt tccgaaatgg gttgtagagg aacaactaga ctacaattca tttcgtaaat  3840
ggtatttaca agtaaaacgt gggaaagccg aaattcctat ttataaaggc ggggaacgtg  3900
ttcaaaaatt cttgacgaaa tctaaaaata atatagaaat gaacgaacta gcggaaatgc  3960
ataaaacaat taattttgct agggaacaaa aaagaaacat tgatctaaat aaaaatatta  4020
cctcacctct agttcgtaat gactatgggg aaaataagga cgaaaagtca gagtatgagt  4080
ttgacgaatg gtatgaaaga ttagaagagt ttaacgatga tatgaatgcg gtagaggaac  4140
tttgtatgaa gtttggaaag atacaaatac cagagaaaaa gcaaaggaag ttatacggac  4200
tttataaaga gtattcttca aaagcgaaag ctatgtgttt ttcaaatgag ggacttccga  4260
```

-continued

```
ttcaagattg gtgtaaaaag acaggatggg acatgaaaga actattaggc gaattaagtt  4320
tcttataata gggagtgacg aaaaatgttg acgccaaggg aacaggatac gttagaatgt  4380
ataagcgggt atatggaaga gtttgggttt gcaccgagtg tgcgagatat ggcgagtcga  4440
atgtacgtaa gtcataagac agcacatcgc tatttaatgc aattggaaag taaaggacga  4500
attaggagag tgcatcaaag acctagagcc atccagttgt tataaggagg ggaaaggtat  4560
gcgtgacaaa ttgctcgact ttatcatcga actatcacaa tctagcaaac aagtcgtaag  4620
caagtcgtat gtcatcgaca ggttaatgca agtaacaaaa gaagactaca aggaactaga  4680
aaagaaaaca gaaaatgcgg aaaaggacta gcaaagttgc tagtcttttt tatttgtcca  4740
aaatgacaca cgtgtgacgg agcggataac aatttcacac aggaaacagc tatgaccatg  4800
attacgaatt cgagctcggt acccggggat cctctagaga ttgtaccgtt cgtatagcat  4860
acattatacg aagttatcga ttttcgttcg tgaatacatg ttataataac tataactaat  4920
aacgtaacgt gactggcaag agatattttt aaaacaatga ataggtttac acttacttta  4980
gttttatgga aatgaaagat catatcatat ataatctaga ataaaattaa ctaaaataat  5040
tattatctag ataaaaaatt tagaagccaa tgaaatctat aaataaacta aattaagttt  5100
atttaattaa caactatgga tataaaatag gtactaatca aaatagtgag gaggatatat  5160
ttgaatacat acgaacaagt taataaagtg aaaaaaatac ttcggaaaca tttaaaaaat  5220
aaccttattg gtacttacat gtttggatca ggagttgaga gtggactaaa accaaatagt  5280
gatcttgact ttttagtcgt cgtatctgaa ccattgacag atcaaagtaa agaaatactt  5340
atacaaaaaa ttagacctat ttcaaaaaaa ataggagata aaagcaactt acgatatatt  5400
gaattaacaa ttattattca gcaagaaatg gtaccgtgga atcatcctcc caaacaagaa  5460
tttatttatg gagaatggtt acaagagctt tatgaacaag gatacattcc tcagaaggaa  5520
ttaaattcag atttaaccat aatgctttac caagcaaaac gaaaaaaataa aagaatatac  5580
ggaaattatg acttagagga attactacct gatattccat tttctgatgt gagaagagcc  5640
attatggatt cgtcagagga attaatagat aattatcagg atgatgaaac caactctata  5700
ttaactttat gccgtatgat tttaactatg gacacgggta aaatcatacc aaaagatatt  5760
gcgggaaatg cagtggctga atcttctcca ttagaacata gggagagaat tttgttagca  5820
gttcgtagtt atcttggaga gaatattgaa tggactaatg aaaatgtaaa tttaactata  5880
aactatttaa ataacagatt aaaaaaatta taaataactt cgtatagcat acattatacg  5940
aacggtagaa tcgtcgacct gcaggcatgc aagcttggca ctggccgtcg ttttacaacg  6000
tcgtgactgg gaaaaccctg gcgttagttc gtgttcgtgc tgacttgcac catatcataa  6060
aaatcgaaac agcaaagaat ggcggaaacg taaaagaagt tatggaaata agacttagaa  6120
gcaaacttaa gagtgtgttg atagtgcagt atcttaaaat tttgtataat aggaattgaa  6180
gttaaattag atgctaaaaa tttgtaatta agaaggagtg attacatgaa caaaaatata  6240
aaatattctc aaaacttttt aacgagtgaa aaagtactca accaaataat aaaacaattg  6300
aatttaaaag aaaccgatac cgtttacgaa attggaacag gtaaagggca ttaaacgacg  6360
aaactggcta aaataagtaa acaggtaacg tctattgaat tagacagtca tctattcaac  6420
ttatcgtcag aaaaattaaa actgaatact cgtgtcactt taattcacca agatattcta  6480
cagtttcaat tccctaacaa acagaggtat aaaattgttg ggagtattcc ttaccattta  6540
agcacacaaa ttattaaaaa agtggttttt gaaagccatg cgtctgacat ctatctgatt  6600
gttgaagaag gattctacaa gcgtaccttg gatattcacc gaacactagg gttgctcttg  6660
cacactcaag tctcgattca gcaattgctt aagctgccag cggaatgctt tcatcctaaa  6720
ccaaaagtaa acagtgtctt aataaaactt acccgccata ccacagatgt tccagataaa  6780
tattggaagc tatatacgta ctttgtttca aaatgggtca atcgagaata tcgtcaactg  6840
tttactaaaa atcagtttca tcaagcaatg aaacacgcca aagtaaacaa tttaagtacc  6900
gttacttatg agcaagtatt gtctattttt aatagttatc tattatttaa cgggaggaaa  6960
taattctatg agtcgctttt gtaaatttgg aaagttacac gttactaaag ggaatgtaga  7020
taaattatta ggtatactac tgacagcttc caaggagcta aagaggtccc tagactcacg  7080
ctgggcataa ctactttgtg acaggagcac atgcaaatgg gtacaaggag gaagtcgaaa  7140
caagacgagt cgtgcaaaga atcgctgaat tatgcgaaga gaacggaatt cactatgcaa  7200
tcactacaga caacgacgga cgcacacaac gccagaattt aaacaacatc atagcgaatt  7260
gtaacagcca tacaagagat cgtgtggacg tagcgattca cttcaaccaa gcaacgtcag  7320
aaaaaggcgg tgtcgaggtt tggtattatg accaatataa tttagcttct aaagtgagcg  7380
aagccgtggc gggtgcgcta ggtatcgcaa accgtggagc gaagcaaggg aaggaattag  7440
cggttctgaa tggacaaat gctcccgcta ttttaataga ggttgcattc ttaaacaatc  7500
cggggaatat gaaagcgtac gaggaacgat ttgaagccgt ttgccgcgct attgtccaaa  7560
gtgttacaga tgtaaatctg aagaactatc aggacttacc tgtcgcaaaa gcggacaaat  7620
attaccgtgt gaacttcggt gactttgaca gctttgattg gttagcgggt gtaaagaaac  7680
gtgtaaacga aatattaccg ggtcacggat gttggattgc ttgtctagcc gggaacgctc  7740
atagaatcct attaggtgac tatggaagcc gagaggaagc acaagccgta attgatagat  7800
tgaatcaaga atttccgggt agtggaattt ggttagaaga attgtaaaat aggaaagagt  7860
tgtggaattg attccatgac tctttttat tttgtttata tcgtgaaaca tagatgttta  7920
tttgtgtcaa tgggtaatat ttcagccaca accatttttg gctgctttgc tgtatgcttc  7980
accagta                                                            7987

SEQ ID NO: 4           moltype = AA  length = 734
FEATURE                Location/Qualifiers
source                 1..734
                       mol_type = protein
                       organism = unidentified
SEQUENCE: 4
MSTTNRKKRR EIKLFTLATE TRGLDGDVFR IGLFDGKQYY TGYTFADVLP VFEKYKAYDC  60
HVYIHNLDFA LSKIIAELRD YAEPTFNNSL FINGNIVTFT ASHIILHDSF RLLPSSLENL  120
CRDFDLLEGG KMDIVDYMEE NNYGIYNVKN RKLNKRLTKG NFFTTVDKDD PVLCEYMEYD  180
CRSLYKILEI VIGLSKLEVE QFINCPTTAS LAKTVYKEQY KKDYKVAIST KQYNHKQLGK  240
GLEAFIRKGY YGGRTEVFTP RIENGYHYDK NSLYPYVMKM AEMPVGYPNV LDNEEAELSF  300
DLWKRRRYGA GFIHAKVHVP EDMYIPILPK KDYTGKLIFP VGKIEGVWTF PELALAEAEG  360
CKIEKIESGV VFEKTAPVFR EFISYFEEIK NTSKGAKRAF SKLMQNALYG KFAMQRERIM  420
YADISERDKL EAEGHTVSEI INDMNGIRME FLEYDGYAMA EYIQPHISAY ITSIARILLF  480
KGLKYAHEKG ILAYCDTDSC ATTTKFPDKM VHDKEYGKWK LEGYVIEGLY FQPKMYAEKA  540
```

-continued

```
INTDGEYEEV LRMKGVPKWV VEEQLDYNSF RKWYLQVKRG KAEIPIYKGG ERVQKFLTKS  600
KNNIEMNELA EMHKTINFAR EQKRNIDLNK NITSPLVRND YGENKDEKSE YEFDEWYERL  660
EEFNDDMNAV EELCMKFGKI QIPEKKQRKL YGLYKEYSSK AKAMCFSNEG LPIQDWCKKT  720
GWDMKELLGE LSFL                                                    734

SEQ ID NO: 5           moltype = DNA  length = 7390
FEATURE                Location/Qualifiers
source                 1..7390
                       mol_type = other DNA
                       organism = unidentified
SEQUENCE: 5
ggatccttcc tcctttaaca tttcccctt tgatttttag atatcactag tttggaccat  60
ttgtcatttc cccctttgat ttaagtgaac aagtttatcc atcaactatc ttaattgagt  120
tagtttgttt atccaataaa ctaactttat ctcatcatat acaaaataaa tgtttatttc  180
aatgtttttt ttagaaaatt tagttataat attagatatg atacttttaa atatctaatt  240
caagcttcaa aaaacaccaa cttagttcgg tggataaaca aaggagtggt tattattcaa  300
attgcagatc aagctttagt aaaaaaaatg aatcaaaaat taatattaga tgaaattttg  360
aagaactccc ctgtctccag ggcaactctc tctgagatta caggattaaa caagtctact  420
gtctcctctc aagtaaatac actgcttgaa aaagatttta tttttgaaat tggggcaggg  480
caatctagag gcggcagaag acctgtaatg cttgttttta ataagaatgc aggctactcg  540
attggtattg atataggagt cgactatctt aacggaattc taaccgactt agaaggaaat  600
attattctcg agaagacttc tgacttgtct agttcttccg ctagtgaagt aaaagagatt  660
ttatttgcac ttattcatgg ttttgtaacc catatgcctg agtcccctta tggtctagtc  720
ggaataggaa tttgtgttcc aggccttgta gatcgtcatc agcaaattat tttcatgcct  780
aacttaaatt ggaatatcaa agatttgcag tttttaattg agagtgagtt taatgttccg  840
gtttttgttg aaaatgaagc taatgcagga gcatacggtg aaaaagtatt tggtatgaca  900
aaaaactatg aaaacatcgt ttacatcagt attaatatcg gaattggaac tggacttgtt  960
attaacaacg aattgtataa aggtgttcag ggtttttctg ggaaatggg tcatatgacg  1020
atagatttta atggacccaa atgcagctgt ggaaatcgag gctgttggga attatatgct  1080
tctgaaaaag cgttactggc ttcgctctct aaagaagaaa agaatatttc tcgaaaagag  1140
attgtggaac gcgcaaataa aaatgatgta gaaatgttaa atgcacttca aaactttggc  1200
ttttatatcg gaattggatt aaccaatatc cttaatacat ttgatataga agctgttatc  1260
ttgagaaatc atataattga atctcatccc attgtttaa atacgattaa aaacgaagtt  1320
tcttctagag tccattctca tttagacaat aaatgtgaac tattgccttc ttcgttagga  1380
aaaaatgcac ctgctttagg agcggtttct atcgttattg attctttttt aagtgttacc  1440
cctataagtt aggagctcct ttattacaaa acgcctgcgc aataacgcag gcgttctgtg  1500
acattaactt cgggcgctct tccgcttcct cgctcactga ctcgctgcgc tcggtcgttc  1560
ggctgcggcg agcggtatca gctcactcaa aggcggtaat acggttatcc acagaatcag  1620
gggataacgc aggaaagaac atgtgagcaa aaggccagca aaaggccagg aaccgtaaaa  1680
aggccgcgtt gctggcgttt ttccataggc tccgcccccc tgacgagcat cacaaaaatc  1740
gacgctcaag tcagaggtgg cgaaacccga caggactata aagataccag gcgtttcccc  1800
ctggaagctc cctcgtgcgc tctcctgttc cgaccctgcc gcttaccgga tacctgtccg  1860
cctttctccc ttcgggaagc gtggcgcttt ctcatagctc acgctgtagg tatctcagtt  1920
cggtgtaggt cgttcgctcc aagctgggct gtgtgcacga accccccgtt cagcccgacc  1980
gctgcgcctt atccggtaac tatcgtcttg agtccaaccc ggtaagacac gacttatcgc  2040
cactggcagc agccactggt aacaggatta gcagagcgag gtatgtaggc ggtgctacag  2100
agttcttgaa gtggtggcct aactacggct acactagaag aacagtattt ggtatctgcg  2160
ctctgctgaa gccagttacc ttcggaaaaa gagttggtag ctcttgatcc ggcaaacaaa  2220
ccaccgctgg tagcggtggt ttttttgttt gcaagcagca gattacgcgc agaaaaaaag  2280
gatctcaaga agatcctttg atcttttcta cggggtctga cgctcagtgg aacgaaaact  2340
cacgttaagg gattttggtc atgagattat caaaaaggat cttcacctag atccttttaa  2400
attaaaaatg aagttttaaa tcaatctaaa gtatatatga gtaaacttgg tctgacagaa  2460
ttaattcctt aaggaacgta cagacggctt aaaagccttt aaaaacgttt ttaaggggtt  2520
tgtagacaag gtaaaggata aacagcaca attccaagaa aaacacgatt tagaacctaa  2580
aaagaacgaa tttgaactaa ctcataaccg agaggtaaaa aaagaacgaa gtcgagatca  2640
gggaatgagt ttataaaata aaaaaagcac ctgaaaaggt gtcttttttt gatggttttg  2700
aacttgttct ttcttatctt gatacatata gaaataacgt cattttatt ttagttgctg  2760
aaaggtgcgt tgaagtgttg gtatgtatgt gttttaaagt attgaaaacc cttaaaattg  2820
gttgcacaga aaaacccat ctgttaaagt tataagtgac taaacaaata actaaataga  2880
tgggggtttc ttttaatatt atgtgtccta atagtagcat ttattcagat gaaaaatcaa  2940
gggttttagt ggacaagaca aaaagtggaa aagtgagacc atggagagaa aagaaaatcg  3000
ctaatgttga ttactttgaa cttctgcata ttcttgaatt taaaaaggct gaaagagtaa  3060
aagattgtgc tgaaatatta gagtataaac aaaatcgtga aacaggcgaa agaaagttgt  3120
atcgagtgtg gttttgtaaa tccaggcttt gtccaatgtg caactggagg agagcaatga  3180
aacatggcat tcagtcacaa aaggttgttg ctgaagttat taaacaaaag ccaacagttc  3240
gttggttgtt tctcacatta acagttaaaa atgtttatga tggcgaagaa ttaaataaga  3300
gtttgtcaga tatggctcaa ggatttcgcc gaatgatgca atataaaaaa attaataaaa  3360
atcttgttgg ttttatgcgt gcaacggaag tgacaataaa taataaagat aattcttata  3420
atcagcacat gcatgtattg gtatgtgtgg aaccaactta ttttaagaat acagaaaact  3480
acgtgaatca aaaacaatgg attcaatttt ggaaaaaggc aatgaaatta gactatgatc  3540
caaatgtaaa agttcaaatg attcgaccga aaaataaata taaatcggat atacaatcgg  3600
caattgacga aactgcaaaa tatcctgtaa aggatacgga ttttatgacc gatgatgaag  3660
aaaagaattt gaaacgtttg tctgatttgg aggaaggttt acaccgtaaa aggttaatct  3720
cctatggtgg tttgttaaaa gaaatacata aaaaattaaa ccttgatgac acagaagaag  3780
gcgatttgat tcatacagat gatgacgaaa aagccgatga agatggattt tctattattg  3840
caatgtggaa ttgggaacgg aaaaattatt ttattaaaga gtagttcaac aaacgggcca  3900
gtttgttgaa gattagatgc tataattgtt attaaaagga ttgaaggatg cttaggaaga  3960
cgagttatta atagctgaat aagaacggtg ctctcggatc cggcgcgccc ctccttgaca  4020
ctgaatttag catgtgatat aattaactta atattctacc caagcttata aaagagcact  4080
```

-continued

```
gttgggcgtg agtggaggcg ccggaaaaaa gcatcgaaaa aaggaggaaa aaaaatgggt  4140
aaggaaaaga ctcacgtttc gaggccgcga ttaaattcca acatggatgc tgatttatat  4200
gggtataaat gggctcgcga taatgtcggg caatcaggtg cgacaatcta tcgattgtat  4260
gggaagcccg atgcgccaga gttgtttctg aaacatggca aaggtagcgt tgccaatgat  4320
gttacagatg agatggtcag actaaactgg ctgacggaat ttatgcctct tccgaccatc  4380
aagcatttta tccgtactcc tgatgatgca tggttactca ccactgcgat ccccggcaaa  4440
acagcattcc aggtattaga agaatatcct gattcaggtg aaaatattgt tgatgcgctg  4500
gcagtgttcc tgcgccggtt gcattcgatt cctgtttgta attgtccttt taacagcgat  4560
cgcgtatttc gtctcgctca ggcgcaatca cgaatgaata acggtttggt tgatgcgagt  4620
gattttgatg acgagcgtaa tggctggcct gttgaacaag tctggaaaga aatgcataag  4680
cttttgccat tctcaccgga ttcagtcgtc actcatggtg atttctcact tgataacctt  4740
atttttgacg aggggaaatt aataggttgt attgatgttg gacgagtcgg aatcgcagac  4800
cgataccagg atcttgccat cctatggaac tgcctcggtg agttttctcc ttcattacag  4860
aaacggcttt ttcaaaaata tggtattgat aatcctgata tgaataaatt gcagtttcat  4920
ttgatgctcg atgagttttt ctaatcagta gatctctgca gtcgcgatga ttaattaatt  4980
cagaacgctc ggttgccgcc gggcgttttt tatgcactga caataaaaag attcttgttt  5040
tcaagaactt gtcatttgta tagttttttt atattgtagt tgttctattt taatcaaatg  5100
ttagcgtgat ttatattttt tttcgccgca tccaatcagt tcagccatcg gctcgcatgc  5160
cggtccaggt acattggcga tattcttttt aagaaaatga gcaaacaaaa acagtcagac  5220
tctgtgtcct gactgttttt gtttgctcat agaatgccga cagcctcata cgccttttcg  5280
actgaagctg ttaaaacacc tcgccctcgt caacaacctc atactccgct tccacagctg  5340
gcgcagccat ttcttcctcc atccaagcgc gagcacggcg agcttgctgc tcggtcatag  5400
agtgcatgcc ttcagcgccc accgcaccac aaacagcagt cataccctca gccggagtga  5460
tgccgaagtg ttcgcaatat ggcttgaaga gttcgcggat tggctggaga tccactggtt  5520
gctccgcctg agcgcgcacc tgttctggct gttgcgcttg atccatttcc tccgcagcgt  5580
acatgccctg aaaagtgtcc gggaacgcga ggcgccaagc agcagccttc gcgcattttt  5640
cgatcataac acccggcatt ttcgcccaat tagatttgcc ggtggaatag tcgtcgagcg  5700
ccacctcagc atacgcagtc tcgcggccat ccttaaagcg aacttccgcc caaccaccga  5760
tgagctcctc acccgccttt ttgtagcacg cagcaccacg tttatgcaca acatcaccgt  5820
cacgcagaac aaccacacca gatttgatac catcatagtt agcatcacga cacgcgcgac  5880
ggttaaaaac ttgataggaa gtaatcatag aagctggagc accgccgtat ttcaccaggt  5940
aagcgtcttt cacaaacgga ttcagacgtt gagtctgaca gagttgcaga aagaggccca  6000
cctcttttc agtagcgttc tcacagatat aacggcgaac atcgtctgga gtaacttgaa  6060
ccgccaggcc agagtcgtca gtgaacttca cgatttggtt catttttatc acctcctttc  6120
tgccaagctt tcatcattat cagaacggaa tgtcatcatc aaagtccatc ggcggctcgt  6180
tagacggcgc tgccggagcg gactgctgcg ggcgagactg cgcgccgccg ctgaactgat  6240
tgccaccctg cggctgctga ggctgacccc aaccgccctg cggctgacca ccaccgatat  6300
tgccacctgc cggagcgcca ccaccctgac gaccacccag catctgcatg gtgccgccaa  6360
cgttcaccac gacttctgtg gtgtagcgat cctgaccgga ttgatcggtc catttacggg  6420
tacgcagctg accttcgata taaacctgag aacctttacg cagatattcg ctcgccactt  6480
ctgccagttt gccgaacagc acaacgcggt gccattcagt ctgttctttc atctcgccgg  6540
tcgctttatc acgccaggat tcggaagtag ccagcgtaat gttggcaact gcgccaccat  6600
ttggcatgta gcgtacttcc gggtcctgac ccagattacc aacgagaata accttgttta  6660
cgcctctgct ggccatgtgt acattcctcc tttacgtttc acctcctttt catcgccatt  6720
gctccccaaa tacaaaacca atttcagcca gtgcctcgtc catttttttcg atgaactccg  6780
gcacgatctc gtcaaaactc gccatgtact tttcatcccg ctcaatcacg acataatgca  6840
ggccttcacg cttcatacgc gggtcatagt tggcaaagta ccaggcattt tttcgcgtca  6900
cccacatgct gtactgcacc tgggccatgt aagctgactt tatggcctcg aaaccaccga  6960
gccggaactt catgaaatcc cgggaggtaa acgggcattt cagttcaagg ccgttgccgt  7020
cactgcataa accatcggga gagcaggcgg tacgcatact ttcgtcgcga tagatgatcg  7080
gggattcagt aacattcacg ccggaagtga attcaaacag ggttctggcg tcgttctcgt  7140
actgttttcc ccaggccagt gctttagcgt taacttccgg agccacaccg gtgcaaacct  7200
cagcaagcag ggtgtggaag taggacattt tcatgtcagg ccacttcttt ccggagcggg  7260
gttttgctat cacgttgtga acttctgaag cggtgatgac gccgagccgt aatttgtgcc  7320
acgcatcatc cccctgttcg acagctctca catcgatccc ggtacgctgc aggataatgt  7380
ccggtgtcat                                                    7390
```

```
SEQ ID NO: 6            moltype = DNA  length = 4660
FEATURE                 Location/Qualifiers
source                  1..4660
                        mol_type = other DNA
                        organism = unidentified
SEQUENCE: 6
aaaattttct aaaattaact attgacaatt tggaaaattt attggaattt ccaaaaggaa  60
aagtgtgaca agatattcca agggtgctat aataggaaat gagttgaaaa cgaacacgcg  120
ttttatagat gttcggtttt tgtaacataa ctgtaacata aaaacatttg cattactggt  180
aactttcggg taatattggt agcagagagg gacaaacggg acaaatcgag acacgataca  240
tactctctat acaagtgaaa agaaggtggt gcatatgtaa tatgagtaaa ctactgactg  300
cgcaagaggt tgcagactta ttgcgtgttc ataaaaagac tatccataga atgatacatt  360
ctggaaagtt agacgcttct aaggtagcaa acaaattcct tattaaagag gaagatgcaa  420
aaggactatt ggaaaataaa aataaaatgg acaattaata ggaggaatat tcaatggaaa  480
acaatactaa acaattaaat aatgaggtta acgaaatcgc ggtagtggac gagcatgtaa  540
atacaaatga catcgtaaca gtggacaagg tgtcaccttc aatctttgaa gcggacggag  600
cgaaggatgt attcttctca tctattcaaa gtaaagatcg taaatcagct atcaaagttt  660
ataatgctat taactctagt gagaatgctc tagcagatca tagaggtgaa gtattagaaa  720
tcacggacat ggttgctcat gctattactc tacaagatga attgacaaaa gaagatgtgg  780
atgcattacg tgttgtttta attgataaga acggtaaagc ataccacgcg gtgtcacaag  840
ggtcgtatc atctattcaa aagattatta gtattgtagg tccagcacct tggaacgagc  900
ctttagaaat tgttccggca gaagtgaaaa cacgtaaagg atttaaaaca ttaactcttc  960
```

```
aactacaagg ctaattttg taacaaatga atgagggtgc acattgtgta tcctcttttt  1020
taaaacataa aaggatggtg cggtcgtgaa cgctattaaa aacttagttc aagtatctat  1080
tcggacaaat gaacgagaac tggaatttgt ctcttttaat ggaatggtgc atttgaagca  1140
aaagttagaa gaagatgaaa catccgtcgt gttaacaaaa gaagagttag acatggttgc  1200
agctatgtct aattttgata atgtgatagc caactttatg aactctatta cagaaaagaa  1260
agccatgtaa gccaaagacc tgtgacctag ttgttacggg tcacatggct ttataagtag  1320
gtgatacaat ggcaaataaa cggttaaaga agaaattaga aacgaaacgt aaaaagtcgt  1380
tacttgtttc agaaggttat agtaagaaag aaacaaagaa gctgaaaggt agagagttag  1440
aaactgttta taaaaagaaa gcgcataata ggaaaaatag agagcgtgct agggaaatag  1500
caaatctagc aagacagtgg ggactttcac cgagtaagtt taattcatgg aaaaagttac  1560
ttccggaaat agagagaata aaaaaagaac aagataggga agcacctttt ctagtaatat  1620
actatcagga ctttacaggt gagacagaca gtaagtttat atatgatttt aaaaagagaa  1680
acaatacaag atcacgtagc caaattacta ggtctataat aggttggttg cagaacgccc  1740
agaacaaact atttttagga agggttgcta tgcggattgt cccaaaacgt gatgtatcta  1800
aaaccaatac actttggaag aatcacggct atgtaaagat atatgaggga caaggaaaag  1860
aacttacaaa actattaaca gcaatagaaa cgataatggt tggtgtttac gacgtaaaag  1920
accgtgacaa gtatttaaag cagttattaa ataatcttcg ttccttacca tataaacaag  1980
cacataggaa cgctaatgag attcagaaga tatatgatac taaatcatat acgaaagaaa  2040
gttgggataa cgatgagtac tactaataga aaaaagcgta gagagattaa actctttacg  2100
ctagatactg aaacacgtgg tttggacggc gacgtgtttc gaattggact attcgatgga  2160
aaacaatact atactggcta tacgtttgca gacgtattac cagtgtttga aaagtacaaa  2220
gcatatgact gtcatgtata tatacataac ctagacttcg acctttccaa gatcatagca  2280
gagttacgtg attatgctga accaacattt aataactcgc tatttatcaa tggtaatata  2340
gtaacgttta ccgcttctca tattatacta catgatagct tccgattgct accgtcttca  2400
cttgaaaact tatgtagaga tttcgacctt ttagaaggtg ggaagatgga tattgtcgat  2460
tatatggaag aaaataatta cggtatttat aatgtaaaaa accgtaaatt gaacaagcga  2520
cttacaaaag gtaatttctt tacaacagta gataaagatg accctgtcct atgtgagtac  2580
atggaatatg attgtcgtag tttatataaa atcttggaaa ttgtaatagg cctatcaaaa  2640
ttagaagttg aacaatttat taattgtccg actacagctt ccctagctaa aacagtttat  2700
aaagaacagt ataagaagga ttataaagtt gctatttcta caaaacaata taatcataaa  2760
caactaggaa aaggtttaga ggcatttatt agaaaaggct actatggagg aagaaccgaa  2820
gtttttacac caagaataga aaacggatac cactatgata aaaatagttt atatccatat  2880
gttatgaaaa tggctgaaat gccagtcgga tacccgaatg tactggataa tgaagaagca  2940
gaactttctt ttgatctatg gaaaagaaga agatatggag caggctttat acatgcgaag  3000
gtacatgtac ccgaagatat gtatattcct atcttaccta aaaaagacta tacaggtaaa  3060
ttgattttcc cagttggtaa aatagaaggt gtttggacat ttccggaact agctttagca  3120
gaagcggaag gttgcaaaat agaaaaaatc gaaagcggtg ttgtatttga gaaaacagca  3180
cctgtctttc gtgaatttat ttcgtatttt gaggaaataa aaaatacaag taaaggtgct  3240
aaacgagcct tttcaaaact tatgcagaat gcgttgtatg gaaaatttgc aatgcagcgg  3300
gaacgaatca tgtatgctga tatttctgag agagataaac ttgaagcaga aggacataca  3360
gtaagcgaga tcatatatga tatgaatgga attcgaatgg aatttttaga gtatgacgga  3420
tatgctatgg ctgaatatat tcaaccacat atttcagcat atattacttc tattgcaaga  3480
attctactat ttaaaggatt gaagtatgcg catgaaaaag gaattttggc ttattgtgat  3540
acggacagtt gtgcaacaac tacgaaattt cctgataaaa tggttcacga taaagagtat  3600
ggaaagtgga agttagaagg gtatgttatt gaaggactct atttccaacc aaaaatgtat  3660
gcggaaaaag ctattaatac cgatggtgaa tatgaggaag tattacgaat gaaaggtgtt  3720
ccgaaatggg ttgtagagga acaactagac tacaattcat ttcgtaaatg gtatttacaa  3780
gtaaaacgtg ggaaagccga aattcctatt tataaaggcg gggaacgtgt tcaaaaattc  3840
ttgacgaaat ctaaaaataa tatagaaatg aacgaactag cggaaatgca taaaacaatt  3900
aattttgcta gggaacaaaa aagaaacatt gatctaaata aaaatattac ctcacctcta  3960
gttcgtaatg actatgggga aaataaggac gaaaagtcag agtatgagtt tgacgaatgg  4020
tatgaaagat tagaagagtt taacgatgat atgaatgcgg tagaggaact ttgtatgaag  4080
tttggaaaga tacaaatacc agagaaaaag caaaggaagt tatacggact ttataaagag  4140
tattcttcaa aagcgaaagc tatgtgtttt tcaaatgagg gacttccgat tcaagattgg  4200
tgtaaaaaga caggatggga catgaaagaa ctattaggcg aattaagttt cttataatag  4260
ggagtgacga aaaatgttga cgccaaggga acaggatacg ttagaatgta taagcgggta  4320
tatggaagag tttgggtttg caccgagtgt gcgagatatg gcgagtcgaa tgtacgtaag  4380
tcataagaca gcacatcgct atttaatgca attggaaagt aaaggacgaa ttaggagagt  4440
gcatcaaaga cctagagcca tccagttgtt ataaggaggg gaaaggtatg cgtgacaaat  4500
tgctcgactt tatcatcgaa ctatcacaat ctagcaaaca agtcgtaagc aagtcgtatg  4560
tcatcgacag gttaatgcaa gtaacaaaag aagactacaa ggaactagaa aagaaaacag  4620
aaaatgcgga aaaggactag caaagttgct agtctttttt                       4660
```

```
SEQ ID NO: 7            moltype = DNA  length = 73
FEATURE                 Location/Qualifiers
source                  1..73
                        mol_type = other DNA
                        organism = unidentified
SEQUENCE: 7
attatgtacc tctactagcc tattaaaata tttacctatt gacacgtaat aacatttatg  60
aaatatgata tac                                                    73
```

```
SEQ ID NO: 8            moltype = DNA  length = 74
FEATURE                 Location/Qualifiers
source                  1..74
                        mol_type = other DNA
                        organism = unidentified
SEQUENCE: 8
tatatcgtga aacatagatg tttatttgtg tcaatgggta atattggtaa aagtgctagt  60
```

```
agggatacat aata                                                    74

SEQ ID NO: 9           moltype = DNA  length = 327
FEATURE                Location/Qualifiers
source                 1..327
                       mol_type = other DNA
                       organism = unidentified
SEQUENCE: 9
ttttttttact aaagcttgat ctgcaatttg aataataacc actcctttgt ttatccaccg  60
aactaagttg gtgtttttttg aagcttgaat tagatattta aaagtatcat atctaatatt  120
ataactaaat tttctaaaaa aaacattgaa ataaacattt attttgtata tgatgagata  180
aagttagttt attggataaa caaactaact caattaagat agttgatgga taaacttgtt  240
cacttaaatc aaagggggaa atgacaaatg gtccaaacta gtgatatcta aaaatcaaag  300
ggggaaatgt taaaggagga aggatcc                                      327

SEQ ID NO: 10          moltype = DNA  length = 8081
FEATURE                Location/Qualifiers
source                 1..8081
                       mol_type = other DNA
                       organism = unidentified
SEQUENCE: 10
ctccaaacaa ctttacacgt aattcgctaa ttcttttcaa atcattcaat tgtctttctg  60
tcagtttcaa attgttaccc tcactttcta tcaatctgct cctacacctc cgttacctcg  120
ccgaccgtac gctcttctca ctcattccat ttcgtttgcc atcagttcac gcgccgtcgt  180
gtcctttgag agtccactcc gtcaccttac cttctgtctg cacttcactt cattcatgtc  240
gctcccttaa gtcgtctact tccggctccg tcgaatacac ttaataaata agtgcccatt  300
tacacagtta actgccatgg gtttcctttc agtcatacaa cgttcaccca agtgaataat  360
aattacaact catacgatta caaaagccgt ttcctaattg ttcagggacc catgcacgga  420
tattctaaat gagtaggtgg cgggcaaact tcagccacac caactacgca tttagtttat  480
cgtgtaaagc ctggggtgcc taatgagtga gctaactcac attaattgcg ttgcgctcac  540
tgcccgcttt ccagtcggga aacctgtcgt gccagctgca ttaatgaatc ggccaacgcg  600
cggggagagg cggtttgcgt attgggcgct cttccgcttc ctcgctcact gactcgctgc  660
gctcggtcgt tcggctgcgg cgagcggtat cagctcactc aaaggcggta atacggttat  720
ccacagaatc aggggataac gcaggaaaga acatgtgagc aaaaggccag caaaaggcca  780
ggaaccgtaa aaaggccgcg ttgctggcgt ttttccatag gctccgcccc cctgacgagc  840
atcacaaaaa tcgacgctca agtcagaggt ggcgaaaccc gacaggacta taaagatacc  900
aggcgtttcc ccctggaagc tccctcgtgc gctctcctgt tccgaccctg ccgcttaccg  960
gatacctgtc cgcctttctc ccttcgggaa gcgtggcgct ttctcatagc tcacgctgta  1020
ggtatctcag ttcggtgtag gtcgttcgct ccaagctggg ctgtgtgcac gaaccccccg  1080
ttcagcccga ccgctgcgcc ttatccggta actatcgtct tgagtccaac ccggtaagac  1140
acgacttatc gccactggca gcagccactg gtaacaggat tagcagagcg aggtatgtag  1200
gcggtgctac agagttcttg aagtggtggc ctaactacgg ctacactaga agaacagtat  1260
ttggtatctg cgctctgctg aagccagtta ccttcggaaa aagagttggt agctcttgat  1320
ccggcaaaca aaccaccgct ggtagcggtg gtttttttgt ttgcaagcag cagattacgc  1380
gcagaaaaaa aggatctcaa gaagatcctt tgatcttttc tacggggtct gacgctcagt  1440
ggaacgaaaa ctcacgttaa gggattttgg tcatgagatt atcaaaaagg atcttcacct  1500
agatcctttt aaattaaaaa tgaagtttta aatcaatcta aagtatatat gagtaaactt  1560
ggtctgacag cgaagttaat gtcacagaac gcctgcgtta ttgcgcaggc gttttgtaat  1620
aaaggagctc ctaacttata ggggtaacac ttaaaaaaga atcaataacg atagaaaccg  1680
ctcctaaagc aggtgcattt tttcctaacg aagaaggcaa tagttcacat ttattgtcta  1740
aatgagaatg gactctagaa gaaacttcgt ttttaatcgt atttaaaaca atgggatgag  1800
attcaattat atgatttctc aagataacag cttctatatc aaatgtatta aggatattgg  1860
ttaatccaat tccgatataa aagccaaagt tttgaagtgc atttaacatt tctacatcat  1920
ttttatttgc gcgttccaca atctctttc gagaaatatt cttttcttct ttagagagcg  1980
aagccagtaa cgctttttca gaagcatata attcccaaca gcctcgattt ccacagctgc  2040
atttgggtcc attaaaatct atcgtcatat gacccatttc cccagaaaaa ccctgaacac  2100
ctttatacaa ttcgttgtta ataacaagtc cagttccaat tccgatatta atactgatgt  2160
aaacgatgtt ttcatagttt tttgtcatac caaatacttt ttcaccgtat gctcctgcat  2220
tagcttcatt ttcaacaaaa accggaacat taaactcact ctcaattaaa aactgcaaat  2280
ctttgatatt ccaatttaag ttaggcatga aaataatttg ctgatgacga tctacaaggc  2340
ctggaacaca aattcctatt ccgactagac cataaggggga ctcaggcata tgggttacaa  2400
aaccatgaat aagtgcaaat aaaatctctt ttacttcact agcggaagaa ctagacaagt  2460
cagaagtctt ctcgagaata atatttcctt ctaagtcggt tagaattccg ttaagatagt  2520
cgactcctat atcaatacca atcgagtagc ctgcattctt attaaaaaca agcattacag  2580
gtcttctgcc gcctctagat tgccctgccc caatttcaaa aataaaatct ttttcaagca  2640
gtgtatttac ttgagaggag acagtagact tgtttaatcc tgtaatctca gagagagttg  2700
ccctggagac aggggagttc ttcaaaattt catctaatat taatttttga ttcatttttt  2760
ttactaaagc ttgatctgca atttgaataa taaccactcc tttgtttatc caccgaacta  2820
agttggtgtt ttttgaagct tgaattagat atttaaaagt atcatatcta atattataac  2880
taaattttct aaaaaaaaca ttgaaataaa catttatttt gtatatgatg agataaagtt  2940
agtttattgg ataaacaaac taactcaatt aagatagttg atggataaac ttgttcactt  3000
aaatcaaagg gggaaatgac aaatggtcca aactagtgat atctaaaaat caaaggggga  3060
aatgttaaag gaggaaggat ccatgagtac tactaataga aaaaagcgta gagagattaa  3120
actctttacg ctagatactg aaacacgtgg tttggacggc gacgtgtttc gaattggact  3180
attcgatgga aaacaatact atactggcta tacgtttgca gacgtattac cagtgtttga  3240
aaagtacaaa gcatatgact gtcatgtata tatacataac ctagacttcg acctttccaa  3300
gatcatagca gagttacgtg attatgctga accaacattt aataactcgc tatttatcaa  3360
tggtaatata gtaacgttta ccgcttctca tattatacta catgatagct tccgattgct  3420
accgtcttca cttgaaaact tatgtagaga tttcgacctt ttagaaggtg ggaagatgga  3480
```

```
tattgtcgat tatatggaag aaaataatta cggtatttat aatgtaaaaa accgtaaatt  3540
gaacaagcga cttacaaaag gtaatttctt tacaacagta gataaagatg accctgtcct  3600
atgtgagtac atggaatatg attgtcgtag tttatataaa atcttggaaa ttgtaatagg  3660
cctatcaaaa ttagaagttg aacaatttat taattgtccg actacagctt ccctagctaa  3720
aacagtttat aaagaacagt ataagaagga ttataaagtt gctatttcta caaaacaata  3780
taatcataaa caactaggaa aaggtttaga ggcatttatt agaaaaggct actatggagg  3840
aagaaccgaa gtttttacac caagaataga aaacggatac cactatgata aaaatagttt  3900
atatccatat gttatgaaaa tggctgaaat gccagtcgga tacccgaatg tactggataa  3960
tgaagaagca gaactttctt ttgatctatg gaaaagaaga agatatggag caggctttat  4020
acatgcgaag gtacatgtac ccgaagatat gtatattcct atcttaccta aaaaagacta  4080
tacaggtaaa ttgattttcc cagttggtaa aatagaaggt gtttggacat ttccggaact  4140
agctttagca gaagcggaag gttgcaaaat agaaaaaatc gaaagcggtg ttgtatttga  4200
gaaaacagca cctgtctttc gtgaatttat ttcgtatttt gaggaaataa aaaatacaag  4260
taaaggtgct aaacgagcct tttcaaaact tatgcagaat gcgttgtatg gaaaatttgc  4320
aatgcagcgg gaacgaatca tgtatgctga tatttctgag agagataaac ttgaagcaga  4380
aggacataca gtaagcgaga tcatatatga tatgaatgga attcgaatgg aatttttaga  4440
gtatgacgga tatgctatgg ctgaatatat tcaaccacat atttcagcat atattacttc  4500
tattgcaaga attctactat ttaaaggatt gaagtatgcg catgaaaaag gaattttggc  4560
ttattgtgat acggacagtt gtgcaacaac tacgaaattt cctgataaaa tggttcacga  4620
taaagagtat ggaaagtgga agttagaagg gtatgttatt gaaggactct atttccaacc  4680
aaaaatgtat gcggaaaaag ctattaatac cgatggtgaa tatgaggaag tattacgaat  4740
gaaaggtgtt ccgaaatggg ttgtagagga acaactagac tacaattcat ttcgtaaatg  4800
gtatttacaa gtaaaacgtg ggaaagccga aattcctatt tataaaggcg gggaacgtgt  4860
tcaaaaattc ttgacgaaat ctaaaaataa tatagaaatg aacgaactag cggaaatgca  4920
taaaacaatt aattttgcta gggaacaaaa aagaaacatt gatctaaata aaaatattac  4980
ctcacctcta gttcgtaatg actatgggga aaataaggac gaaaagtcag agtatgagtt  5040
tgacgaatgg tatgaaagat tagaagagtt taacgatgat atgaatgcgg tagaggaact  5100
ttgtatgaag tttggaaaga tacaaatacc agagaaaaag caaaggaagt tatacggact  5160
ttataaagag tattcttcaa aagcgaaagc tatgtgtttt tcaaatgagg gacttccgat  5220
tcaagattgg tgtaaaaaga caggatggga catgaaagaa ctattaggcg aattaagttt  5280
cttataagga ttgaaggatg cttaggaaga cgagttatta atagctgaat aagaacggtg  5340
ctctcggatc cggcgcgccc ctccttgaca ctgaatttag catgtgatat aattaactta  5400
atattctacc caagcttata aaagagcact gttgggcgtg agtggaggcg ccggaaaaaa  5460
gcatcgaaaa aaggaggaaa aaaaatgggt aaggaaaaga ctcacgtttc gaggccgcga  5520
ttaaattcca acatggatgc tgatttatat gggtataaat gggctcgcga taatgtcggg  5580
caatcaggtg cgacaatcta tcgattgtat gggaagcccg atgcgccaga gttgtttctg  5640
aaacatggca aaggtagcgt tgccaatgat gttacagatg agatggtcag actaaactgg  5700
ctgacggaat ttatgcctct tccgaccatc aagcatttta tccgtactcc tgatgatgca  5760
tggttactca ccactgcgat ccccggcaaa acagcattcc aggtattaga agaatatcct  5820
gattcaggtg aaaatattgt tgatgcgctg gcagtgttcc tgcgccggtt gcattcgatt  5880
cctgtttgta attgtccttt taacagcgat cgcgtatttc gtctcgctca ggcgcaatca  5940
cgaatgaata acggtttggt tgatgcgagt gattttgatg acgagcgtaa tggctggcct  6000
gttgaacaag tctggaaaga aatgcataag cttttgccat tctcaccgga ttcagtcgtc  6060
actcatggtg atttctcact tgataacctt atttttgacg aggggaaatt aataggttgt  6120
attgatgttg gacgagtcgg aatcgcagac cgataccagg atcttgccat cctatggaac  6180
tgcctcggtg agttttctcc ttcattacag aaacggcttt ttcaaaaata tggtattgat  6240
aatcctgata tgaataaatt gcagtttcat ttgatgctcg atgagttttt ctaatcagta  6300
gatctctgca gtcgcgatga ttaattaatt cagaacgctc ggttgccgcc gggcgttttt  6360
tatgcactga caataaaaag attcttgttt tcaagaactt gtcatttgta tagttttttt  6420
atattgtagt tgttctattt taatcaaatg ttagcgtgat ttatattttt tttcgcctcg  6480
acatcatctg cccagatgcg gatgtgcatc tcctaatcaa taagactaca ttttcgaaac  6540
ataaccgtta cttcaactca aacatattcc ctttttgatt caattgttgc tgcgttacat  6600
tttcaaacat catactcaac atttgttgca tctttggcat ttgttccaac ataacctttt  6660
gattcacata attctctaaa gctaaatgaa ctaaagtgct tttcggtaca ccactttctt  6720
tgctatactc gtccaaccaa tcatttaact ttttactgat acgtgtatta acacgaacca  6780
tttcactcat ctaatcacct cttgtatatc gtactacata aatataacat cagtttaaac  6840
acaatatcaa cactaagata caccagaaca atgtaaaagt gggactctat ccgctattaa  6900
tataaacaag ttaagaaaaa caaaaagaga gcatcatatt gacaccctct tgacacacag  6960
agaagcacac gctaatatca taaacgagta tagttcttaa tattttctaa tatagataac  7020
caacagtcct gtagaatggg gtccaccgcc aagtgatcca tttcttcaag ggcttttttt  7080
atactctctt tagttctacg agggaactct ttcatatcca tagttccatt agaataacaa  7140
atcaaacaag cttttaatgc ccctttaaca ttattcaaat taaaaatcga gaatgtataa  7200
gattcatcaa tactaaacgg aggactcttc cttatttcgt ctaccactac accgtcagag  7260
tctctccaac tatactcaat acgagtcaaa ttctcttctt ctatcattct tttaaaatga  7320
ttatataact cctttttctt atcatatatc ttcaaatatc catctttatt tctatttcca  7380
taataaacag ttcctttatg tctatcctgt tgctttcctg ttttactata agacacaata  7440
tcactcatat gacgctctat atcaaaagca atatccatac cataaaccac tcgcttatta  7500
gacttcaaaa ctgcatttaa cgtatgaaaa acggtttcaa acactttttc ataactatct  7560
ttttgcaact cgttatttc aaatttagaa gggttaaaat caactttcat atcatagcta  7620
tctttttcct tttccgaatt atgtttccac cctatataaa ctgcaccttc accatatcca  7680
atatgtataa ctctatgata atctctaaca gacgtcccat gttctgacct aataggtgta  7740
ttcggtaaaa aaatctgctt tgacgatatt ttagttaaaa catcactaaa ttgtttctct  7800
gttacatctt tatacttaat cattagccta tccaaataaa cttgcataaa atctatcccg  7860
ctccttattt tttattaaac atgtcatttt gtacacgatt ttcggctatt agaatgtccg  7920
aaaatgtctt cgccacattt ctacaattta cccacacatt gaattatact gttcaatctc  7980
tatcgtgact tcaaaaattt ctaattgccc taaataagaa ctaatagcat tatccaataa  8040
aaactcaaca ttctctggat caactacact ttcaccagga a                      8081
```

SEQ ID NO: 11 moltype = DNA length = 24

```
FEATURE                Location/Qualifiers
source                 1..24
                       mol_type = other DNA
                       organism = unidentified
SEQUENCE: 11
acggacagtt gtgcaacaac tacg                                       24

SEQ ID NO: 12          moltype = DNA  length = 41
FEATURE                Location/Qualifiers
source                 1..41
                       mol_type = other DNA
                       organism = unidentified
SEQUENCE: 12
gaaattgtta tccgctccgt cacacgtgtg tcattttgga c                    41

SEQ ID NO: 13          moltype = DNA  length = 42
FEATURE                Location/Qualifiers
source                 1..42
                       mol_type = other DNA
                       organism = unidentified
SEQUENCE: 13
cacgtgtgac ggagcggata acaatttcac acaggaaaca gc                   42

SEQ ID NO: 14          moltype = DNA  length = 35
FEATURE                Location/Qualifiers
source                 1..35
                       mol_type = other DNA
                       organism = unidentified
SEQUENCE: 14
gaacacgaac taacgccagg gttttcccag tcacg                           35

SEQ ID NO: 15          moltype = DNA  length = 39
FEATURE                Location/Qualifiers
source                 1..39
                       mol_type = other DNA
                       organism = unidentified
SEQUENCE: 15
ggaaaaccct ggcgttagtt cgtgttcgtg ctgacttgc                       39

SEQ ID NO: 16          moltype = DNA  length = 42
FEATURE                Location/Qualifiers
source                 1..42
                       mol_type = other DNA
                       organism = unidentified
SEQUENCE: 16
gccagtttcg tcgtttaatg ccctttacct gttccaattt cg                   42

SEQ ID NO: 17          moltype = DNA  length = 43
FEATURE                Location/Qualifiers
source                 1..43
                       mol_type = other DNA
                       organism = unidentified
SEQUENCE: 17
ggtaaagggc attaaacgac gaaactggct aaaataagta aac                  43

SEQ ID NO: 18          moltype = DNA  length = 45
FEATURE                Location/Qualifiers
source                 1..45
                       mol_type = other DNA
                       organism = unidentified
SEQUENCE: 18
gtagttatgc ccagcgtgag tctagggacc tctttagctc cttgg                45

SEQ ID NO: 19          moltype = DNA  length = 32
FEATURE                Location/Qualifiers
source                 1..32
                       mol_type = other DNA
                       organism = unidentified
SEQUENCE: 19
cctagactca cgctgggcat aactactttg tg                              32

SEQ ID NO: 20          moltype = DNA  length = 25
FEATURE                Location/Qualifiers
source                 1..25
                       mol_type = other DNA
                       organism = unidentified
SEQUENCE: 20
caattacggc ttgtgcttcc tctcg                                      25
```

-continued

```
SEQ ID NO: 21          moltype = DNA  length = 53
FEATURE                Location/Qualifiers
source                 1..53
                       mol_type = other DNA
                       organism = unidentified
SEQUENCE: 21
tgttaaagga ggaaggatcc atgagtacta ctaatagaaa aaagcgtaga gag        53

SEQ ID NO: 22          moltype = DNA  length = 54
FEATURE                Location/Qualifiers
source                 1..54
                       mol_type = other DNA
                       organism = unidentified
SEQUENCE: 22
gcatccttca atccttataa gaaacttaat tcgcctaata gttctttcat gtcc       54

SEQ ID NO: 23          moltype = DNA  length = 38
FEATURE                Location/Qualifiers
source                 1..38
                       mol_type = other DNA
                       organism = unidentified
SEQUENCE: 23
gtttcttata aggattgaag gatgcttagg aagacgag                         38

SEQ ID NO: 24          moltype = DNA  length = 58
FEATURE                Location/Qualifiers
source                 1..58
                       mol_type = other DNA
                       organism = unidentified
SEQUENCE: 24
catggatcct tcctccttta acatttcccc ctttgatttt tagatatcac tagtttgg   58
```

BACTERIAL CONTINUOUS EVOLUTION SYSTEM, ORTHOGONAL ERROR-PRONE DNA POLYMERASE, AND CONTINUOUS EVOLUTION METHOD

This application is a Continuation application of PCT/CN2023/092743, filed on May 8, 2023, which claims priority to Chinese Patent Application No. 202211021222.2, filed on Aug. 24, 2022, which is incorporated by reference for all purposes as if fully set forth herein.

A Sequence Listing XML file named "10015_0138.xml" created on Nov. 20, 2023, and having a size of 52,451 bytes, is filed concurrently with the specification. The sequence listing contained in the XML file is part of the specification and is herein incorporated by reference in its entirety.

FIELD OF THE INVENTION

The present invention relates to the field of biotechnologies, and particularly to a bacterial continuous evolution system, an orthogonal error-prone DNA polymerase, and a continuous evolution method.

DESCRIPTION OF THE RELATED ART

Directed evolution technology realizes the development of new gene expression elements or high-efficiency enzymes through library construction and high-throughput screening, and is currently widely used in enzyme engineering, metabolic engineering and other fields. However, the traditional directed evolution method requires the initial construction of an in-vitro library, which not only has low throughput, but also often requires the consumption of large time and cost. Therefore, many continuous evolution methods have been developed to overcome this difficulty. The key to continuous evolution is to realize random mutation of a target DNA sequence in vivo, which is not only simple to operate, but also can greatly improve the throughput of the library. However, at present, a continuous evolution method satisfying the following four conditions has not been developed in bacteria, that is, including all mutant types, realizing long-DNA-fragment mutation, having good continuity and having simple operation. The orthogonal DNA replication system previously developed in yeast can meet the four key characteristics. However, it is still a huge challenge to develop such a system in bacteria. Therefore, to provide a basis for the development of enzyme engineering, metabolic engineering and other fields, the present invention accomplishes a continuous evolution method based on an orthogonal linear gene expression vectors in bacteria, namely *Bacillus thuringiensis.*

SUMMARY OF THE INVENTION

To solve the above technical problems, the present invention provides a continuous evolution method based on a bacterial orthogonal linear gene expression vector, which is obtained by combining an orthogonal DNA replication system with an orthogonal error-prone DNA polymerase and can meet four key characteristics, that is, including all mutant types, realizing the long-DNA-fragment mutation, having good continuity and simple operation. The continuous evolution method can be applied to the evolution of a target DNA sequence.

A first object of the present invention is to provide a bacterial continuous evolution system including a linear plasmid and a mutant DNA polymerase.

The linear plasmid includes a DNA replication and control gene cluster, a promoter and a target gene, in which the DNA replication and control gene cluster has a nucleotide sequence as shown in SEQ ID NO. 6.

The mutant DNA polymerase is obtained by mutation from a DNA polymerase having an amino acid sequence as shown in SEQ ID NO. 1. The mutation is selected from:

- mutation of aspartate at position 18 to alanine, and mutation of aspartate at position 70 to alanine (D18A/D70A);
- mutation of aspartate at position 18 to alanine, mutation of aspartate at position 70 to alanine, and mutation of tyrosine at position 442 to asparagine (D18A/D70A/Y442N);
- mutation of aspartate at position 18 to alanine, mutation of aspartate at position 70 to alanine, and mutation of leucine at position 521 to serine (D18A/D70A/L521S);
- mutation of aspartate at position 18 to alanine, mutation of aspartate at position 70 to alanine, and mutation of valine at position 191 to phenylalanine (D18A/D70A/V191F);
- mutation of aspartate at position 18 to alanine, mutation of aspartate at position 70 to alanine, and mutation of valine at position 199 to phenylalanine (D18A/D70A/V199F); or
- mutation of aspartate at position 18 to alanine, mutation of aspartate at position 70 to alanine, mutation of leucine at position 403 to lysine, mutation of methionine at position 404 to isoleucine, and mutation of glutamine at position 405 to methionine (D18A/D70A/L403K/M404I/Q405M).

Particularly, the DNA polymerase as shown in SEQ ID NO.1 has a sequence shown below:

```
MSTTNRKKRREIKLFTLDTETRGLDGDVFRIGLFDGKQYYTGYTFADVLP

VFEKYKAYDCHVYIHNLDFDLSKIIAELRDYAEPTFNNSLFINGNIVTFT

ASHIILHDSFRLLPSSLENLCRDFDLLEGGKMDIVDYMEENNYGIYNVKN

RKLNKRLTKGNFFTTVDKDDPVLCEYMEYDCRSLYKILEIVIGLSKLEVE

QFINCPTTASLAKTVYKEQYKKDYKVAISTKQYNHKQLGKGLEAFIRKGY

YGGRTEVFTPRIENGYHYDKNSLYPYVMKMAEMPVGYPNVLDNEEAELSF

DLWKRRRYGAGFIHAKVHVPEDMYIPILPKKDYTGKLIFPVGKIEGVWTF

PELALAEAEGCKIEKIESGVVFEKTAPVFREFISYFEEIKNTSKGAKRAF

SKLMQNALYGKFAMQRERIMYADISERDKLEAEGHTVSEIIYDMNGIRME

FLEYDGYAMAEYIQPHISAYITSIARILLFKGLKYAHEKGILAYCDTDSC

ATTTKFPDKMVHDKEYGKWKLEGYVIEGLYFQPKMYAEKAINTDGEYEEV

LRMKGVPKWVVEEQLDYNSFRKWYLQVKRGKAEIPIYKGGERVQKFLTKS

KNNIEMNELAEMHKTINFAREQKRNIDLNKNITSPLVRNDYGENKDEKSE

YEFDEWYERLEEFNDDMNAVEELCMKFGKIQIPEKKQRKLYGLYKEYSSK

AKAMCFSNEGLPIQDWCKKTGWDMKELLGELSFL.
```

Preferably, the linear plasmid further comprises a resistance gene terminated early by a stop codon, which provides an approach to determine the mutation rate of the linear plasmid vector. In an example of the present invention, an expression frame encoding erythromycin resistance protein terminated early by the stop codon "TAA" is used, which has a nucleotide sequence as shown in SEQ ID NO. 2.

Preferably, in an embodiment of the present invention, the linear plasmid includes a DNA replication and control gene cluster and an expression frame encoding erythromycin resistance protein early terminated by stop codon "TAA" and has a nucleotide sequence as shown in SEQ ID NO. 3.

Preferably, Further, the linear plasmid further comprises a replication origin at both ends. From 5' end to 3' end, the elements includes a left replication origin, a DNA replication and control gene cluster, a promoter, a target gene and a right replication origin sequentially. The left replication origin has a nucleotide sequence as shown in SEQ ID NO. 7, and the right replication origin has a nucleic sequence as shown in SEQ ID NO. 8.

Specifically, the left replication origin has a nucleotide sequence shown below:

attatgtacctctactagcctattaaaatatttacctattgacacgtaataacatttatgaaatatgatatac; and the right replication origin has a nucleotide sequence shown below:

Tatatcgtgaaacatagatgtttatttgtgtcaatgggtaatattggtaaaagtgctagtagggatacataata.

Preferably, the linear plasmid has pBMB-ESC as a vector.

Preferably, the linear plasmid vector is derived from the genome of double-stranded linear DNA lysogenic phage GIL16.

Preferably, the linear plasmid vector is engineered by homologous recombination.

Preferably, the linear plasmid vector is replicated by the orthogonal DNA polymerase (the amino acid sequence of the wild-type polymerase is as shown in SEQ ID NO. 1) of GIL16, and the replication is orthogonal to the genome. The "orthogonal" means that the DNA polymerase for replicating the linear plasmid cannot be used to replicate the genome, and the DNA polymerase of the host cannot initiate the replication of the linear plasmid.

Preferably, the promoter on the linear plasmid is any promoter suitable for host cells, such as an inducible promoter. In one embodiment of the present invention, a xylose-inducible promoter, such as $P_{xylA}$, is used.

Preferably, the xylose-inducible promoter $P_{xylA}$ has a nucleotide sequence as shown in SEQ ID NO. 9.

Preferably, the mutant DNA polymerase is controlled to express by an inducible promoter. In one embodiment of the present invention, a xylose-inducible promoter, such as $P_{xylA}$, is used.

Preferably, in an embodiment of the present invention, the mutant DNA polymerase is linked to a vector backbone pBMB.

A second object of the present invention is to provide a cell including the bacterial continuous evolution system.

Preferably, the bacterium is *Bacillus thuringiensis*, including but not limited to, *Bacillus thuringiensis* HD-1 (GenBank No: CP001903), *Bacillus thuringiensis* JW-1 (GenBank No: CP045030), and others.

A third object of the present invention is to provide an orthogonal error-prone mutant DNA polymerase, obtained by mutation from a DNA polymerase having an amino acid sequence as shown in SEQ ID NO. 1. The mutation is selected from:

- mutation of aspartate at position 18 to alanine, and mutation of aspartate at position 70 to alanine (D18A/D70A, M6);
- mutation of aspartate at position 18 to alanine, mutation of aspartate at position 70 to alanine, and mutation of tyrosine at position 442 to asparagine (D18A/D70A/Y442N, M17);
- mutation of aspartate at position 18 to alanine, mutation of aspartate at position 70 to alanine, and mutation of leucine at position 521 to serine (D18A/D70A/L521S, M18);
- mutation of aspartate at position 18 to alanine, mutation of aspartate at position 70 to alanine, and mutation of valine at position 191 to phenylalanine (D18A/D70A/V191F, M19);
- mutation of aspartate at position 18 to alanine, mutation of aspartate at position 70 to alanine, and mutation of valine at position 199 to phenylalanine (D18A/D70A/V199F, M20); or
- mutation of aspartate at position 18 to alanine, mutation of aspartate at position 70 to alanine, mutation of leucine at position 403 to lysine, mutation of methionine at position 404 to isoleucine, and mutation of glutamine at position 405 to methionine (D18A/D70A/L403K/M404I/Q405M, M21).

Preferably, the error-prone DNA polymerase includes three mutations D18A, D70A and Y442N (having an amino acid sequence as shown in SEQ ID NO. 4), and the mutation rate is $6.82\times10^{-7}$ per generation per cell per base, which is 6,700 times the genomic mutation rate.

Preferably, the error-prone DNA polymerase is obtained by structural prediction and reasonably designed mutation of AlphaFold2.

A fourth object of the present invention is to provide a gene encoding the orthogonal error-prone mutant DNA polymerase.

A fifth object of the present invention is to provide an expression vector carrying the gene encoding the orthogonal error-prone mutant DNA polymerase.

A sixth object of the present invention is to provide a cell expressing the orthogonal error-prone mutant DNA polymerase. The cell may be a bacterial cell, a fungal cell, a plant cell, an animal cell or the like.

A seventh object of the present invention is to provide use of the bacterial continuous evolution system, the cell including the bacterial continuous evolution system, the mutant DNA polymerase, the gene encoding the mutant DNA polymerase, the expression vector carrying the gene encoding the mutant DNA polymerase, and the cell expressing the mutant DNA polymerase in the food and biological fields, particularly in the continuous evolution and error-prone replication of bacteria.

Preferably, the use includes adding an inducer to a cell culture, to realize the error-prone replication and random mutation of a target DNA sequence. The target DNA sequence includes, but is not limited to, a promoter, a ribosome binding site and a methanol utilization gene cluster.

An eighth object of the present invention is to provide a continuous evolution method based on a bacterial orthogonal error-prone DNA polymerase, including the step of introducing the linear plasmid and the mutant DNA polymerase into a cell (bacteria). The construction of a random mutation library of a target protein (encoded by a target gene) and use of directed evolution of high-throughput screening are realized by orthogonal error-prone replication of a linear plasmid by the DNA polymerase in a cell.

Preferably, the mutant DNA polymerase is regulated to express by an inducible promoter, and then induced to express by adding an inducer under culture conditions. In the evolution method of the present invention, by inducing the opening and closing of mutant DNA polymerase expression, switching between a linear plasmid error-prone mutation process and a high-fidelity replication process is realized, so as to control the continuous evolution process.

Preferably, the concentration of the inducer is 0.01-100 g/L.

By virtue of the above solution, the present invention has the following advantages.

By constructing a continuous evolution method based on a bacterial orthogonal linear gene expression vector in the present invention, the efficient continuous evolution of a target DNA sequence is realized. The present invention has the following advantages: including all mutation types, realizing the long-DNA-fragment mutation (the theoretical mutation frame length is greater than the phage genome length, that is, 15000 bp), having good continuity and simple operation. The orthogonal error-prone DNA polymerase is obtained by predicting the structure by AlphaFold2, reasonably designing, and determining the mutation rate. The mutation rate of the optimal mutant reaches $6.82\times10^{-7}$ per generation per cell per base, which is 6,700 times the genomic mutation rate, and will not cause a significant increase in the genomic mutation rate.

The above description is only a summary of the technical solutions of the present invention. To make the technical means of the present invention clearer and implementable in accordance with the disclosure of the specification, the preferred embodiments of the present invention will be described in detail with reference to the accompanying drawings.

BRIEF DESCRIPTION OF THE DRAWINGS

To make the disclosure of the present invention more comprehensible, the present invention will be further described in detail by way of specific embodiments of the present invention with reference the accompanying drawings, in which FIG. 1 shows a conceptual diagram of continuous evolution method based on an orthogonal linear gene expression vector.

DETAILED DESCRIPTION OF THE PREFERRED EMBODIMENTS

The present invention will be further described below with reference to the accompanying drawings and specific examples, so that those skilled in the art can better understand and implement the present invention; however, the present invention is not limited thereto.

Materials and methods involved in the examples:

*Bacillus thuringiensis* HD-1 (GenBank No: CP001903).

Green fluorescent protein (GFP) under GenBank Accession No. AF324408.1.

LB medium (g/L): tryptone 10, powdery yeast 5, and NaCl 10.

SG buffer: containing sucrose 93.1 g and glycerol 150 ml in each liter.

0.1 M PBS: containing $K_2HPO_4$ 1.4 g and $KH_2PO_4$ 0.52 g, in each 100 mL.

1 M $MgCl_2$: containing $MgCl_2\cdot6H_2O$ 20.33 g, in each 100 mL.

EP buffer: containing SG buffer 1 L, 0.1 M PBS 5 mL, and 1.0 M $MgCl_2$ 500 μL, in each liter.

Determination method of green fluorescent protein expression: 200 μL diluted fermentation liquor per well was added to a 96-well plate, and detected by Cytation3 cell imaging microplate reader (Bio-TeK Co., Ltd), with an excitation wavelength of 488 nm, an emission wavelength of 523 nm and a gain of 60.

FIG. 1 shows a conceptual diagram of continuous evolution method based on an orthogonal linear gene expression vector.

Example 1. Electrorotation of *Bacillus thuringiensis*

Preparation of competent cells: A single colony was picked up into 5 mL LB medium and activated and cultured at 30° C. overnight. Then it was transferred to fresh LB medium according to an inoculation amount of 1/100, cultured at 30° C. and 220 r/min until the OD600 was about 1.0-1.3 (about 2 hrs), and then cooled in ice bath for 10-30 min. The whole preparation process of competent cells and transformation were carried out at low temperature. After cooling, the cell suspension was centrifuged at 5000 r/5 min and 4° C. for 5 min. The cells was collected and the supernatant was discarded. Then, under the same conditions, the cells were washed twice with precooled EP buffer and once with precooled SG buffer. Finally, the cells were re-suspended in SG buffer (about 1.5 mL), to give an OD600 value of the competent cells of about 50-70. The competent cells were packaged in a centrifuge tube in 50 μL/tube and stored at −80° C. for later use; or packaged in a centrifuge tube in 500 μL/tube, and subpackaged in site immediately before use.

Electrorotation process: 1 tube of competent cells was placed on ice, and added with 3-5 μL plasmid DNA (the plasmid concentration was more than 100 ng/μL, and *Escherichia coli* JM110 was required to be used as the cloning host, otherwise the plasmid will be cleaved by a restriction endonuclease, resulting in transformation failure). The cells were mixed well by slightly shaking, allowed to stand in an ice bath for 10-30 min, and added to a 1 mm precooled electrorotation cup. After electrorotation at 1.25 kV, 500 μL LB medium preheated at 37° C. was quickly added. The cells were recovered and cultured at 37° C. and 220 r/min for 2 hrs, then coated on a resistant plate, and cultured overnight in an incubator at 37° C.

Example 2. Determination of Mutation Rate of DNA Polymerase and Construction of Host A helper plasmid pBMB-ESC (having a sequence as shown in SEQ ID NO. 5) was constructed to realize the efficient recombination of *Bacillus thuringiensis* HD-1. Specifically, Exo (double-stranded DNA 5'-3' exonuclease), EcoSSB (*E. Coli* derived single-stranded DNA binding protein) and CspRecT (DNA annealing protein) were induced to express by xylose on this plasmid to form a single-stranded DNA by the DNA fragment and enable high-efficiency annealing in the cells.

The linear plasmid integration frame was constructed by fusion PCR. Firstly, a recombinant frame with a homologous arm length of 500-1000 bp was designed, for example, a linear plasmid (having a nucleotide sequence as shown in SEQ ID NO. 3) containing an expression frame encoding erythromycin resistance protein (having a nucleotide sequence as shown in SEQ ID NO. 2) early terminated by the stop codon "TAA". The specific operation was as follows. Using the primers HD-TE-1F: acggacagttgtgcaacaactacg (SEQ ID NO. 11), and HD-TE-1R: gaaattgttatccgctccgtcacacgtgtgtcattttggac (SEQ ID NO. 12), the left arm was amplified. Using the primers HD-TE-2F: cacgtgtgacggagcggataacaatttcacacaggaaacagc (SEQ ID NO. 13), and HD-TE-2R: gaacacgaactaacgccagggttttcccagtcacg (SEQ ID NO. 14), the expression frame of spectinomycin resistance protein was amplified. Using the primers HD-TE-3F: ggaaaaccctggcgttagttcgtgttcgtgctgacttgc (SEQ ID NO. 15), and HD-TE-3R: gccagtttcgtcgttTaatgccctttacctgttccaatttcg (SEQ ID NO. 16), the expression frame of erythromycin antibiotic resistance protein was amplified. Using the primers HD-TE-4F: ggtaaagggcattAaacgacgaaactggctaaaataagtaaac (SEQ ID NO. 17), and HD-TE-4R: gtagttatgcccagcgtgagtctagggacctctttagctccttgg (SEQ ID NO. 18), the expression frame of erythromycin antibiotic resistance protein was amplified. The TAA stop condon was introduced. Using the primers HD-TE-5F: cctagactcacgctgggcataactactttgtg (SEQ ID NO. 19), and HD-TE-5R: caattacggcttgtgcttcctctcg (SEQ ID NO. 20), the right arm was amplified.

After purification of the obtained DNA fragment, the corresponding linear plasmid/genome integration operation was as follows. Firstly, competent cells of the strain containing pBMB-ESC plasmid were prepared. Xylose was added with a final concentration of 3% when the OD600 of the cell suspension was about 0.5, and the cells were further cultured until the OD600 was about 1.0-1.3. The other operations were the same as those in the electroporation of plasmid. During electroporation, the DNA fragment needed to be relatively simple. 5 μL DNA fragment with a concentration of above 200 ng/μL was added, and then cultured for 3 hrs. The other operations were the same as those in the electrotransformation of plasmid. Finally, by the DNA integration frame, the recombination and editing of the genome of the prophage GIL16 was realized. A linear plasmid containing the expression frame encoding erythromycin resistance protein terminated by the stop codon "TAA" was constructed. Under the same conditions, the strain containing complete erythromycin resistance gene could grow in the presence of erythromycin, and the strain containing erythromycin resistance gene early terminated by TAA stop codon could not grow in the presence of chloramphenicol. To induce the expression of DNA polymerase, the GIL16 DNA polymerase was amplified using the primers pDNAP-1F: tgTTAAAGGAGGAAGGATCCatgagtactactaatagaaaaaagcgtagagag (SEQ ID NO. 21), and pDNAP-1R: gcatccttcaatccttataagaaacttaattcgcctaatagttctttcatgtcc (SEQ ID NO. 22); and the pBMB pasmid vector containing a xylose-inducible promoter was amplified using the primers pDNAP-2F: gtttcttataaggattgaaggatgcttaggaagacgag (SEQ ID NO. 23), and HD-TE-2R: catGGATCCTTCCTCCTTTAAcatttcccccttttgatttttagatatcactagtttgg (SEQ ID NO. 24). The plasmid pBMB-ODNAP (SEQ ID NO. 10) was constructed after Gibson assembly.

Example 3. Determination of Mutation Rate of Various Orthogonal Mutant DNA Polymerase By reasonable design, 24 mutant DNA polymerase were obtained (Table 1, the GIL16 orthogonal DNA polymerase has an amino acid sequence as shown in SEQ ID No. 1).

TABLE 1

Determination of mutation rate of various mutant DNA polymerase

| Name of mutant | Reasonable mutation | Mutation rate (per generation per cell per base) |
|---|---|---|
| GIL16DNA Polymerase | | $2.52 \times 10^{-9}$ |
| M1 | T19I | $3.87 \times 10^{-9}$ |
| M2 | N66D | $1.57 \times 10^{-7}$ |
| M3 | N66D L403R | $1.47 \times 10^{-7}$ |
| M4 | H65R | $2.17 \times 10^{-7}$ |
| M5 | H65R L403R | $1.26 \times 10^{-7}$ |
| M6 | D18A D70A | $4.98 \times 10^{-7}$ |
| M7 | Y137A | $4.69 \times 10^{-9}$ |
| M8 | N66D L403K | $2.23 \times 10^{-7}$ |
| M9 | L113T | $7.44 \times 10^{-9}$ |
| M10 | V199F L403K L521S | $3.18 \times 10^{-9}$ |
| M11 | L117V L403K Y442N | $3.38 \times 10^{-8}$ |
| M12 | L113W L403K Y442N | $6.70 \times 10^{-9}$ |
| M13 | L117V L403K | $3.21 \times 10^{-8}$ |
| M14 | L113W L403K | $3.32 \times 10^{-8}$ |
| M15 | L403K L521S | $5.57 \times 10^{-9}$ |
| M16 | D18A D70A L403K | $3.34 \times 10^{-8}$ |
| M17 | D18A D70A Y442N | $6.82 \times 10^{-7}$ |
| M18 | D18A D70A L521S | $5.15 \times 10^{-7}$ |
| M19 | D18A D70A V191F | $3.02 \times 10^{-7}$ |
| M20 | D18A D70A V199F | $4.11 \times 10^{-7}$ |
| M21 | D18A D70A L403K M404I Q405M | $2.50 \times 10^{-7}$ |
| M22 | D18A D70A A399N F400V S401I L403K M404I Q405M | $1.40 \times 10^{-10}$ |
| M23 | D18A D70A L403K M404I Q405M L521S | $1.12 \times 10^{-8}$ |
| M24 | D18A D70A L403K Y442N S401I L403K M404I Q405M L521S | $4.38 \times 10^{-9}$ |

Then, the recombinant *Bacillus thuringiensis* constructed in Example 2 was induced by pBMB-ODNAP plasmid to express 24 additional mutants, and induced by adding 5% xylose. After inoculation at 1/1000, the cells were cultured to saturated biomass, and then diluted and coated on a plate. The proportion of resistant colonies in the total cells was counted. For each mutant, 17 replicates were set, and the fluctuation of the final result was analyzed by FALCOR tool (https://lianglab.brocku.ca/FALCOR/). The final mutation rate μ (s.p.b.) was calculated. The mutation rate is calculated by the formula μ (s.p.b.)=f/(R×C), where f is the result calculated by FALCOR, R is the unique mutant species that restores erythromycin resistance gene, and c is the copy number of plasmid. According to the sequencing result, when mutation of TAA to AAA/CAA/TTA/TAT/TAC allows the strain acquire erythromycin resistance, so R=5/3. Among the 24 mutants, M17 (having an amino acid sequence as shown in SEQ ID No. 4) has the largest mutation rate, $6.82\times10^{-7}$ per generation per cell per base.

The mutation rate of wild-type orthogonal DNA polymerase was determined through the following steps. 5% xylose was added to induce the wild-type DNA polymerase to express extracellularly; and after inoculation at 1/1000, the cells were cultured to saturated biomass, then diluted and coated on a plate, and the proportion of resistant colonies in the total cells was counted. The mutation frequency of wild-type orthogonal DNA polymerase is determined to be $2.52\times10^{-9}$ per generation per cell per base.

Example 4. Control of Mutation Rate and Mutation Frequency of Target DNA by Adding Various Concentrations of Xylose The recombinant *Bacillus thuringiensis* with M17 mutant constructed in Example 3 was cultured for 10 hrs in 700 μL LB medium in a 96-well deep plate at 37° C. and 750 rpm, to obtain a seed culture. Then the seed culture was transferred in an inoculation amount of 0.1% to 200 μL LB medium with various concentrations of xylose, so that the final concentration of xylose in various wells was 0.00 g/L to 50 g/L. 17 parallel replicates were set for each concentration, and cultured at 37° C. and 750 rpm for 24 hrs. Under the same conditions, the mutation rate of the control group without xylose is $2.59\times10^{-8}$; and after adding 0.01, 0.05, 0.1, 0.25, 0.5, 1, 2.5, 5, 10, 30, 50 g/L xylose, the average values of mutation rate and mutation frequency are shown in Table 2 respectively.

TABLE 2

| Mutation rate and mutation frequency of target DNA after adding various concentrations of xylose | | | | | | | | | | | | |
|---|---|---|---|---|---|---|---|---|---|---|---|---|
| | Xylose concentration g/L | | | | | | | | | | | |
| | 0.00 | 0.01 | 0.05 | 0.10 | 0.25 | 0.50 | 1.0 | 2.50 | 5.0 | 10.0 | 30.0 | 50.0 |
| Mutation frequency ($\times10^{-7}$) | 0.26 | 0.43 | 0.54 | 0.47 | 0.79 | 2.31 | 4.07 | 5.68 | 6.26 | 5.36 | 5.31 | 5.32 |
| Mutation frequency ($\times10^{-5}$) | 0.09 | 0.11 | 0.14 | 0.14 | 0.24 | 0.51 | 1.01 | 1.78 | 2.22 | 2.54 | 3.26 | 2.89 |

Comparative Example 1. Determination of Genomic Mutation Rate of Strain

The method for determining the genomic mutation rate was the same as the method for determining the orthogonal DNA polymerase, except that xylose was not added, and the mutant gene selected was genomic RpoB protein. When the genome RpoB protein had the following mutations, the strain would acquire rifampin resistance: V135F (gtt-ttt), Q137R (cag-cgg), Q468R (cag-cgg), Q468K (cag-aag), Q468L (cag-ctg), H481D (cac-gac), H481P (cac-ccc), H481Y (cac-tac), H481R (cac-cgc), S486Y (tct-tat), S486F (tct-ttt), and L488S (tta-tca). Therefore, R=12/3. After the seed culture of the strain was inoculated at 1/1000, the cells were cultured to saturated biomass, and then diluted and coated on a plate. The proportion of resistant colonies in the total cells was counted. Finally, the genomic mutation frequency is $1.02\times10^{-10}$ per generation per cell per base. Therefore, it can be calculated that the mutation rate of orthogonal error-prone DNA polymerase is 6700 times that of the genomic mutation frequency.

In addition, the genomic mutation rate of recombinant *Bacillus thuringiensis* with M17 mutant constructed in Example 3 was determined by the same method. The result is $1.45\times10^{-10}$. The significance analysis shows that no significant increase in the genomic mutation rate is caused.

Apparently, the above-described embodiments are merely examples provided for clarity of description, and are not intended to limit the implementations of the present invention. Other variations or changes can be made by those skilled in the art based on the above description. The embodiments are not exhaustive herein. Obvious variations or changes derived therefrom also fall within the protection scope of the present invention.

What is claimed is:

1. A bacterial continuous evolution system, comprising a linear plasmid and a mutant DNA polymerase, wherein the linear plasmid comprises a DNA replication and control gene cluster, a promoter and a target gene, in which the DNA replication and control gene cluster has a nucleotide sequence as shown in SEQ ID NO.6;

the mutant DNA polymerase is obtained by mutation from a DNA polymerase having an amino acid sequence as shown in SEQ ID NO.1, wherein the mutation is selected from:

mutation of aspartate at position 18 to alanine, and mutation of aspartate at position 70 to alanine;

mutation of aspartate at position 18 to alanine, mutation of aspartate at position 70 to alanine, and mutation of tyrosine at position 442 to asparagine;

mutation of aspartate at position 18 to alanine, mutation of aspartate at position 70 to alanine, and mutation of leucine at position 521 to serine;

mutation of aspartate at position 18 to alanine, mutation of aspartate at position 70 to alanine, and mutation of valine at position 191 to phenylalanine;

mutation of aspartate at position 18 to alanine, mutation of aspartate at position 70 to alanine, and mutation of valine at position 199 to phenylalanine; or mutation of aspartate at position 18 to alanine, mutation of aspartate at position 70 to alanine, mutation of leucine at position 403 to lysine, mutation of methionine at position 404 to isoleucine, and mutation of glutamine at position 405 to methionine.

2. The bacterial continuous evolution system according to claim 1, wherein the linear plasmid further comprises a resistance gene terminated early by a stop codon.

3. The bacterial continuous evolution system according to claim 1, wherein the mutant DNA polymerase is controlled to express by an inducible promoter.

4. An isolated cell comprising the bacterial continuous evolution system according to claim 1.

5. A orthogonal error-prone mutant DNA polymerase, obtained by mutation from a DNA polymerase having an amino acid sequence as shown in SEQ ID NO.1, wherein the mutation is selected from:

mutation of aspartate at position 18 to alanine, and mutation of aspartate at position 70 to alanine;

mutation of aspartate at position 18 to alanine, mutation of aspartate at position 70 to alanine, and mutation of tyrosine at position 442 to asparagine;

mutation of aspartate at position 18 to alanine, mutation of aspartate at position 70 to alanine, and mutation of leucine at position 521 to serine;

mutation of aspartate at position 18 to alanine, mutation of aspartate at position 70 to alanine, and mutation of valine at position 191 to phenylalanine;

mutation of aspartate at position 18 to alanine, mutation of aspartate at position 70 to alanine, and mutation of valine at position 199 to phenylalanine; or mutation of aspartate at position 18 to alanine, mutation of aspartate at position 70 to alanine, mutation of leucine at position 403 to lysine, mutation of methionine at position 404 to isoleucine, and mutation of glutamine at position 405 to methionine.

6. A gene encoding the orthogonal error-prone mutant DNA polymerase according to claim 5.

7. An expression vector carrying the gene according to claim 6.

8. An isolated cell expressing the orthogonal error-prone mutant DNA polymerase according to claim 5.

9. A continuous evolution method based on a bacterial orthogonal error-prone DNA polymerase, comprising a step of transforming the linear plasmid and the mutant DNA polymerase in claim 1 into a cell.

* * * * *